United States Patent
Shiigi et al.

(10) Patent No.: US 7,087,798 B2
(45) Date of Patent: Aug. 8, 2006

(54) PROCESS FOR PREPARATION OF SPIROFLUORENOLS

(75) Inventors: Hirohumi Shiigi, Shunan (JP); Noriyuki Fukada, Shunan (JP); Kenji Tanaka, Shunan (JP); Masao Yamaguchi, Shunan (JP)

(73) Assignee: Tokuyama Corporation, Yamaguchi (JP)

( * ) Notice: Subject to any disclaimer, the term of this patent is extended or adjusted under 35 U.S.C. 154(b) by 0 days.

(21) Appl. No.: 10/526,016

(22) PCT Filed: Dec. 13, 2002

(86) PCT No.: PCT/JP02/13091

§ 371 (c)(1),
(2), (4) Date: Aug. 10, 2005

(87) PCT Pub. No.: WO2004/022514

PCT Pub. Date: Mar. 18, 2004

(65) Prior Publication Data

US 2006/0025636 A1 Feb. 2, 2006

(30) Foreign Application Priority Data

Aug. 29, 2002 (JP) ............................. 2002-249970
Nov. 6, 2002 (JP) ............................. 2002-323086

(51) Int. Cl.
C07C 39/205 (2006.01)
C07C 39/12 (2006.01)
C07C 37/11 (2006.01)

(52) U.S. Cl. ...................... 568/715; 568/707; 568/716; 568/714; 568/808; 568/809

(58) Field of Classification Search ................ 568/715, 568/716, 707, 714, 809, 808
See application file for complete search history.

(56) References Cited

FOREIGN PATENT DOCUMENTS

| EP | 1 054 010 A1 | 11/2000 |
|---|---|---|
| JP | 10-508031 A | 8/1998 |
| JP | 2000034418 A | 2/2000 |
| JP | 2001192378 A1 | 7/2001 |
| WO | WO 96/14596 A1 | 5/1996 |

OTHER PUBLICATIONS

Ried, Walter et al., Reactions with cyclopentadienones XVI. Reaction products of 1,1-diaryl-2-propyn-1-ols and 1-methoxy-1, 1-diaryl-2propynes with cyclopentadienones Chemische Berichte, 1969, vol, 102, No. 6, pp. 1904 to 1916.

Primary Examiner—Elvis O. Price
(74) Attorney, Agent, or Firm—Birch, Stewart, Kolasch & Birch, LLP

(57) ABSTRACT

A spirofluorenol such as 3',9'-dimethoxy-5'-hydroxyspiro[(1H-cyclopent[d,e,f]phenanthrene)-1,7'-benzo[c]fluorene] is produced by protecting a hydroxyl group bonded to a particular fluorenone compound such as 3,9-dimethoxy-5-hydroxybenzo[c]fluorene-7-one with "a substituted silyl group in which the sum of carbon atoms of substituents bonded to a silicon atom is 5 to 12", such as a t-butyldimethylsilyl group, then, reacting the fluorenone compound with a particular organometal compound such as 1-lithiophenanthrene so as to be transformed into a spiro form and, then, removing the protection therefrom. This method makes it possible to efficiently produce the spirofluorenol which is useful as a starting material for producing photochromic compounds.

7 Claims, No Drawings

PROCESS FOR PREPARATION OF SPIROFLUORENOLS

BACKGROUND OF THE INVENTION 1. (Field of the Invention)

The present invention relates to a method of producing a spirofluorenol compound useful as a starting material for producing a photochromic compound.

2. (Description of the Related Art)

Recently, the chromene derivatives, especially spiroindenonaphthopyranes draw much attention as photochromic compounds for their fast color developing-fading rates, easy color tone controllability and high color fastness. In these spiroindenonaphthopyranes, spiroketal type compounds (International Patent Publication No. 10-508031), biphenyl type spiro-compounds and phenanthrene type spiro-compounds (Japanese Unexamined Patent Publication (Kokai) No. 2000-34418 and No. 2001-192378) are known. In particular, the latter two compounds feature high color-developing sensitivity, fast fading rate and excellent color fastness.

It has been known that these compounds are obtained by modifying the properly substituted indenonaphthopyrane-one, prepared by several steps, represented by the following formula (5) (Japanese Unexamined Patent Publication (Kokai) No. 2000-34418 and No. 2001-192378). However, according to the above method, a strict purification must be needed to obtain desired developing color tone because a trace of impurity may exhibits photochromic properties and may developing undesired color tone when using the indenonaphthopyrane-one, it exhibits photochromic properties by itself, as the intermediate.

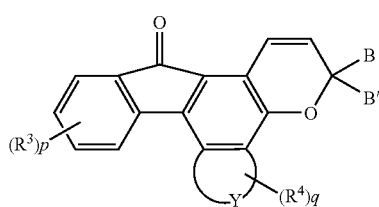

(5)

On the other hand, it has been known another method, which is little likely to form photochromic impurities, for producing desired chromene derivatives from spirofluorenol (Japanese Unexamined Patent Publication (Kokai) No. 2001-192378).

According to the above method, a hydroxyfluorenone having a phenolic hydroxyl group is reacted with a Grignard reagent, and then reacted under acidic condition to form spirofluorenol. As a result, excess amounts of Grignard reagent is required to complete the former reaction.

SUMMARY OF THE INVENTION

Therefore, the present invention provides an efficient method of producing a spirofluorenol which is useful as a starting material for producing the photochromic compounds.

By protecting a hydroxyl group of the hydroxyfluorenone, the present inventors have attempted to decrease the amount of organometal reagents such as Grignard reagent used during the course of producing the spirofluorenols, and have studied the effect of various protecting groups, As a result, the inventors have discovered that only a particular protecting group can be introduced with a high selectivity and a high conversion, and that the particular protecting group is durable under the condition of the next step, and that the particular protecting group can be easily removed in good yield, and have finished the invention.

According to the present invention, this is provided a method of producing a spirofluorenol compound represented by the following formula (1),

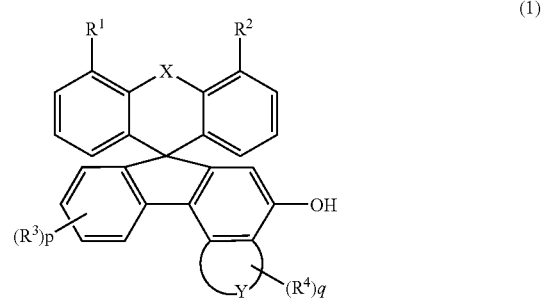

(1)

by protecting a hydroxyl group bonded to a fluorenone compound represented by the following formula (2),

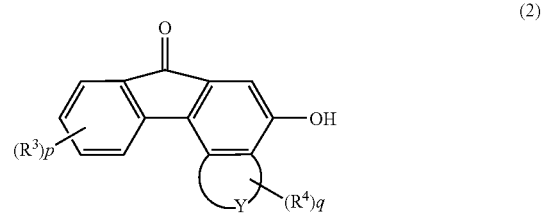

(2)

with a protecting group which is a substituted silyl group in which the sum of carbon atoms of substituents bonded to a silicon atom is 5 to 12, then, reacting the fluorenone compound with an organometal compound represented by the following formula (3),

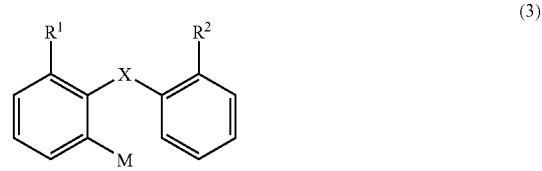

(3)

wherein M is Li, MgCl, MgBr, MgI or CuLi, to thereby obtain a hydroxy-arylfluorenol of which the hydroxyl group is protected with said protecting group, and transforming the obtained hydroxy-arylfluorenol into a spiro form and removing the protection therefrom, wherein in the above formulas (1) to (3):

X is either a single bond or a divalent group selected from the following group A;

Y is a group forming an aromatic hydrocarbon cyclic group or an unsaturated heterocyclic group together with two carbon atoms of a benzo ring;

when X is a single bond, $R^1$ and $R^2$ are, respectively, hydrogen atoms or monovalent groups selected from the following group B, or are bonded together to form a divalent group selected from the following group A (except, -Z- and —CR$^5$R$^6$—);

when X is a group selected from the group A, R$^1$ and R$^2$ are, respectively, hydrogen atoms or monovalent groups selected from the following group B;

R$^3$ and R$^4$ are, respectively, hydrogen atoms or monovalent groups selected from the following group B; and p and q are, independently from each other, integers of 0 to 3;

group A:

-Z-, —(CR$^5$R$^6$)$_n$—, —(CR$^5$R$^6$)$_m$-Z-, -Z-(CR$^5$R$^6$)$_l$-Z-, —(CR$^5$R$^6$)$_a$-Z-(CR$^5$R$^6$)$_b$—, —(CR$^5$=CR$^6$)$_k$—, and CR$^5$=N— wherein -Z- is —O—, —S— or —NR$^5$—, R$^5$ and R$^6$ are, independently from each other, hydrogen atoms, or monovalent groups selected from the following group B, wherein when there are a plurality of -Z-, R$^5$ or R$^6$ in one group, the plurality of -Z-, R$^5$ or R$^6$ may be different from each other, and a, b, k and l are, independently from each other, integers of 1 to 4, and m and n are, independently from each other, integers of 1 to 6;

group B:

alkyl group, aralkyl group, substituted or unsubstituted aryl group, hydroxy group, alkoxy group, aralkoxy group, amino group, monosubstituted amino group, disubstituted amino group, cyano group, nitro group, halogen atom, trufluoromethyl group, substituted or unsubstituted heterocyclic group having a bond on a carbon atom or on a nitrogen atom, and substituted or unsubstituted condensed heterocyclic group, aromatic hydrocarbon ring or hetero ring in condensed thereto and having a bond on a carbon atom or on a nitrogen atom.

DETAILED DESCRIPTION OF THE INVENTION (Object Product to be Produced)

A spirofluorenol compound represented by the above formula (1) produced by a production method of the present invention is useful as a starting material for the synthesis of a photochromic compound that comprises a chromene derivative.

In the above formula (1), X is either a single bond or a divalent group selected from the above group A.

Further, groups in the above group B serve not only as R$^5$ or R$^6$ in the group A but also as R$^1$, R$^2$, R$^3$ or R$^4$ in the above formula (1). Preferred examples of the group in the group B include alkyl groups having 1 to 6 carbon atoms, such as methyl group, ethyl group, isopropyl group, t-butyl group and cyclohexyl group; aralkyl groups having 7 to 20 carbon atoms, such as benzyl group, phenethyl group and trityl group; substituted or unsubstituted aryl groups, such as phenyl group, naphthyl group and alkoxyphenyl group; hydroxyl group; alkoxy groups having 1 to 6 carbon atoms, such as methoxy group and t-butoxy group; aralkoxy groups having 7 to 20 carbon atoms, such as benzyloxy group and trityloxy group; amino group; monosubstituted amino groups having 1 to 6 carbon atoms, such as methylamino group and cyclohexylamino group; disubstituted amino groups having 1 up to 20 carbon atoms, such as dimethylamino group and dicyclohexylamino group; cyano group; nitro group; halogen atoms, such as chlorine atom and bromine atom; trifluoromethyl group; substituted or unsubstituted heterocyclic groups, such as 2-oxazolyl group, 4-morpholino group, and 2,2,6,6-tetramethyl-1-piperidino group; and substituted or unsubstituted condensed heterocyclic groups, such as 2-benzoxazolyl group, 1-benzotriazolyl group, 9-carbazolyl group and 8-quinolyl group.

When X is a single bond in the above formula (1), R$^1$ and R$^2$ are, respectively, hydrogen atoms, groups selected from the group B, or groups that are bonded together to form a group represented by the group A. That is, when X is a single bond, the compound of the above formula (1) possesses a 9,9'-spirobifluorene skeleton. For example, when R$^1$ and R$^2$ are bonded together, then, —CR$^5$=CR$^6$— that is formed, the compound possesses a spiro[fluorene-9,1'-(1H-cyclopent[d,e,f]phenanthrene)] skeleton. However, it never takes place from the steric requirement that R$^1$ and R$^2$ are bonded together to form -Z- (i.e., —O—, —S— or —NR$^5$—) or —CR$^5$R$^6$—.

Further, when X is a divalent group selected from the group A, R$^1$ and R$^2$ are, respectively, hydrogen atoms or groups selected from the group B. In this case, the compound represented by the above formula (1) possesses a spiro[fluorene-9,9'-xanthene] skeleton (when X is —O—), a spiro[fluorene-9,9'-(9,10-dihydroacridine] skeleton (when X is —NH—), or a spiro[fluorene-9,9'-(9,10-dihydroanthracene] skeleton (when X is —CH$_2$—). However, there is no particular steric limitation on R$^1$ and R$^2$.

In the above formula (1), Y is a group that forms an aromatic hydrocarbon group or an unsaturated heterocyclic group together with two carbon atoms of a benzo ring. When Y forms an aromatic hydrocarbon group, the compound of the formula (1) possesses, for example, a benzofluorenol skeleton or a naphthofluorenol skeleton. When Y forms an unsaturated heterocyclic group, the compound of the formula (1) possesses, for example, a furofluorenol skeleton or an indolofluorenol skeleton. Here, the place and direction of ring condensation are quite arbitrary.

In the above formula (1), further, R$^3$ and R$^4$ are monovalent groups in the above group B, and p and q representing the numbers of R$^3$ and R$^4$ are integers of 0 to 3, respectively. When p or q is 2 or 3, i.e., when R$^3$ or R$^4$ is existing in a plural number, the plurality of R$^3$ or R$^4$ may be different from each other.

(Production of the Spirofluorenol Compounds)

Starting Materials:

To produce the spirofluorenol compound of the above-mentioned formula (1) according to the present invention, first, a hydroxyl group bonded to a fluorenone compound represented by the formula (2),

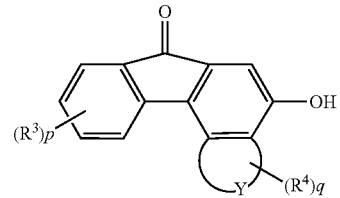

(2)

wherein Y, R$^3$, R$^4$, p and q are as defined in the formula (1), is protected with a protecting group which is a substituted silyl group. Here, when the compound of the formula (2) contains an amino group or a monosubstituted amino group, the amino group or the monosubstituted amino group, too, is protected with the substituted silyl group in addition to the hydroxyl group. The hydroxyl group to be protected is not limited to the one bonded to the 2-position of the fluorenone ring but includes a hydroxyl group bonded to any other position. When $R^3$ or $R^4$ is a hydroxyl group, an amino group or a monosubstituted amino group, then, the above group is protected with the substituted silyl group in addition to the hydroxyl group bonded to the 2-position of the fluorenone ring. Hereinafter, the group that is to be protected is often called to-be-protected functional group.

There is no particular limitation on the hydroxyfluorenone used as the starting material provided it is the one represented by the above formula (2). Desirably, however, the hydroxyfluorenone used as the starting material is the one in which Y is a condensed benzo ring (i.e., the one having a hydroxybenzofluorenone skeleton) from the standpoint of performance of the object photochromic compound. From the standpoint of performance of the object photochromic compound, further, it is desired that $R^3$ and $R^4$ are alkyl groups having 1 to 6 carbon atoms, such as methyl groups, ethyl groups, isopropyl groups, t-butyl groups and cyclohexyl groups; aralkyl groups having 7 to 20 carbon atoms, such as benzyl groups, phenethyl groups and trityl groups; substituted or unsubstituted aryl groups, such as phenyl groups, naphthyl groups and alkoxyphenyl groups; hydroxy groups; alkoxy groups having 1 to 6 carbon atoms, such as methoxy groups and t-butoxy groups; or aralkoxy groups having 7 to 20 carbon atoms, such as benzyloxy groups and trityloxy groups; and p and q are 0 or 1.

Concrete examples of the hydroxyfluorenone of the formula (2) that can be favorably used in the present invention include 3-methoxy-5-hydroxybenzo[c]fluorene-7-one, 9-methoxy-5-hydroxybenzo[c]fluorene-7-one and 3,9-dimethoxy-5-hydroxybenzo[c]fluorene-7-one.

Introduction of Protecting Groups:

In the present invention, a substituted silyl group is used as a protecting group for protecting the above-mentioned to-be-protected functional group. Here, the greatest feature resides in that the sum of carbon atoms of three substituents bonded to a silicon atom is 5 to 12. That is, by using the substituted silyl group having a large steric hindrance as a protecting agent, the selectivity and the conversion are both maintained high at the time of introducing the protecting group, the protecting group is not removed in the next step of reaction, the yield is improved at the time of removing the protection and, as a result, a spirofluorenol which is a desired compound is efficiently produced.

Various protecting groups have been proposed for protecting the hydroxyl group, such as methyl group, benzyl group, as well as methoxymethyl group and tetrahydropyranyl group which are of the acetal type; acetyl group and benzoyl group which are of the ester type; benzyloxycarbonyl group and t-butoxycarbonyl group which are of the carbonate type; and trimethylsilyl group which is of the silyl ether type. When the methyl group is used as the protecting group, however, the alkoxy group is destroyed in the step of removing the protecting group if $R^3$ or $R^4$ of hydroxyfluorenone is an alkoxy group such as methoxy group, which, therefore, cannot serve as a general method of production. When the benzyl group is used as the protecting group, the benzyl is introduced not only to the hydroxyl group to which the protecting group is to be introduced but also to the molecular skeleton. In the step of removing the protecting group (for removing protection), therefore, side reactions take place much, such as destroying the alkoxy group and reducing the molecular skeleton, which is not efficient. The protection group of the acetal type involves problems, too, in regard to selectivity at the time of introducing the protecting group. The protecting groups of the ester type and of the carbonate type cannot withstand the reaction condition in the next step. Even the protecting group of the silyl ether type cannot withstand the reaction of the next step if it has a sterically simple structure like the trimethylsilyl group and cannot, hence, be used.

There is no particular limitation on the substituted sily group used as a protecting group in the invention provided it satisfies a condition that the sum of carbon atoms of three substituents is 5 to 12. It is, however, particularly desired to use t-butyldimethylsilyl group, triisopropylsilyl group or 2-methyl-3,3-dimethyl-2-butyldimethylsilyl group from such a standpoint that a silylating agent used for introducing the protecting group is easily available and is effective as will be described later.

The silylating agent used for introducing the protecting group is a compound in which the substituted silyl group is bonded to an eliminating group, and is a compound represented by, for example, the following formula (6),

$$E\text{-}SiR^7R^8R^9 \qquad (6)$$

wherein E is an eliminating group, and $R^7$, $R^8$ and $R^9$ are alkyl groups, the sum of carbon atoms of the alkyl groups being 5 to 12.

As the eliminating group, there can be exemplified a halogen atom, an azide group, an alkoxy group, an arylsulfonyloxy group and a trialkylsilylamino group having the total number of carbon atoms of not smaller than 5. Among the silylating agents represented by the above formula (6), it is desired to use chlorinated silicon compound such as t-butyldimethylsilyl chloride, triisopropylsilyl chloride, or 2-methyl-3,3-dimethyl-2-butyldimethylsilyl chloride from the standpoint of availability.

That is, upon reacting the above silylating agent with the hydroxyfluorenone of the formula (2), a protecting group which is the substituted silyl group is introduced to protect the to-be-protected functional group as represented by the hydroxyl group.

Though there is no particular limitation on the reaction conditions at the time of protection, a solvent is usually used, and a tertiary amine compound is added to a mixed solution of the hydroxyfluorenone and the silylating agent to conduct the reaction while trapping the acid formed during the reaction thereby to introduce the protecting group. Or, a hydroxyl group of the hydroxyfluorenone is reacted with sodium hydride, potassium t-butoxide, sodium hydroxide or potassium hydroxide to form an alkali metal salt thereof which is, then, reacted with the silylating agent to introduce the protecting group. It is allowable to use the above two methods in combination to carry out the reaction, as a matter of course.

There is no particular limitation on the solvent used here provided it does not react with the silylating agent. Examples include aromatic hydrocarbons such as toluene and xylene; chlorinated hydrocarbons such as dichloromethane and chloroform; acyclic or cyclic ethers such as diethyl ether and tetrahydrofurane; nitriles such as acetonitrile and butyronitrile; acyclic or cyclic amide such as dimethylformamide and N-methylpyrrolidone; acyclic or cyclic sulfoxide such as dimethyl sulfoxide and sulforane; or a mixed solvent thereof.

As the tertiary amine compound, though there is no particular limitation, there can be used acyclic or cyclic aliphatic tertiary amines such as triethylamine and n-methylmorpholine; aromatic tertiary amines such as dimethyl aniline and methyl diphenylamine; and heterocyclic tertiary amines such as pyridine and 4-dimethylaminopyridine. Among them, it is desired to use a tertiary amine compound having a structure represented by the following formula (4),

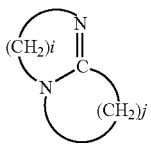

(4)

wherein i is an integer of 2 to 4, and j is an integer of 3 to 6, such as 1,8-diazabicyclo[5,4,0]undeca-7-ene or 1,7-diazabicyclo[4,3,0]nona-6-ene from the standpoint of high selectivity and high conversion. It is further allowable to use the tertiary amine compound represented by the above formula (4) in a catalytic amount in combination with other tertiary amine compounds.

There is thus obtained a hydroxyfluorenone of which the to-be-protected functional group such as a hydroxyl group is protected. This compound can be isolated and refined according to conventional methods but can also be directly used for the next reaction.

Reaction with an Organometal Compound:

According to the production method of the present invention, the hydroxyfluorenone protected with the substituted silyl group obtained above is reacted with an organometal compound represented by the formula (3),

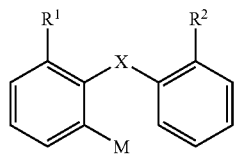

(3)

wherein M is Li, MgCl, MgBr, MgI or CuLi, and X, $R^1$ and $R^2$ are as defined in the formula (1), to prepare a hydroxyl-protected-arylfluorenol. In carrying out the reaction, the to-be-protected functional group such as the hydroxyl group bonded to the 2-position of the fluorenone ring has been protected by the substituted silyl group, and does not take part in the reaction with the organometal compound, and only the carbonyl group (C=O) reacts with the organometal compound. Therefore, the obtained hydroxy-protected-arylfluorenol is expressed by, for example, the following formula (7), and the hydroxyl group and the like groups have been protected by the substituted silyl groups.

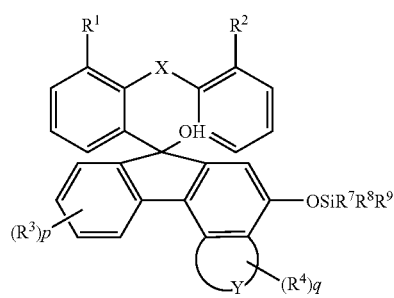

(7)

In the above formula (7), when $R^3$ or $R^4$ is a hydroxyl group, amino group or a monosubstituted amino group, then, this group, too, is protected by the protecting group (substituted silyl group, —$SiR^7R^8R^9$).

The organometal compound used for the above reaction is obtained by reacting a halogen compound having a molecular structure corresponding to the molecular skeleton of the formula (3) with an organolithium compound such as butyl lithium, or with lithium metal, magnesium metal or alkyl copper lithium compound. The organometal compound can be further produced even by reacting an organolithium compound having a molecular structure corresponding to the molecular skeleton of the formula (3) with a copper compound.

The reaction of the hydroxyfluorenone of which the hydroxyl group is protected with the organosilyl compound is carried out by reacting the organometal compound produced as described above with the hydroxyfluorenone of which the hydroxyl group and the like groups have been protected without isolating the organometal compound. There is no particular limitation on the solvent used for the reaction provided it does not react with the organometal compound, and there can be used acyclic or cyclic aliphatic hydrocarbon such as hexane or cyclohexane; aromatic hydrocarbon such as toluene or xylene; or acyclic or cyclic ether such as diethylether or tetrahydrofurane; or a mixed solvent thereof. Though there is no particular limitation, the reaction temperature may be from –10° C. to about a boiling point of the solvent, and the reaction time may be from 0.5 hours to about 10 hours, which may be determined while making sure the progress of the reaction. After the reaction, the reaction product is quenched with water to obtain a hydroxy-arylfluorenol of which the hydroxyl group and the like groups are protected. The thus obtained hydroxy-arylfluorenol of which the hydroxyl group and the like groups are protected can be isolated and refined by conventional methods, but can also be directly used for the next reaction.

Transforming Into a Spiro Form and Removing the Protection:

In the present invention, the "hydroxy-arylfluorenol of which the hydroxyl group and the like groups are protected" obtained as described above is transformed into a spiro form under an acidic condition to obtain a spirofluorenol of which the to-be-protected functional group such as hydroxyl group and the like groups are protected with the substituted silyl groups.

An acid is used for establishing an acidic condition. As the acid, there can be used known acids without limitation, e.g., inorganic acids such as sulfuric acid and phosphoric acid; organic acids such as p-toluenesulfonic acid and trifluoroacetic acid; inorganic Lewis acids such as aluminum chloride, titanium tetrachloride, silicon tetrachloride, tin chloride and iron chloride; and solid acids such as acidic alumina and acidic ion-exchange resin. There can be further used a dehydrating agent that forms an acid upon reacting with water, such as phosphorus pentoxide, phosphorus pentachloride, thionyl chloride and sulfuryl chloride. The amount of the acid that is used differs depending upon its kind and there is no particular limitation. In general, however, the acid is used in an amount of 0.01 to 1000 parts by weight and, more preferably, 1 to 50 parts by weight per 100 parts by weight of the hydroxy-arylfluorenol.

The spiro-reaction is conducted under the acidic condition usually in a solvent. There is no particular limitation on the solvent used here provided it does not react with the acid that is used, and there can be desirably used an acyclic or cyclic aliphatic hydrocarbon such as hexane or cyclohexane, aromatic hydrocarbon such as toluene or xylene, chlorinated hydrocarbon such as dichloromethane or chloroform, cyclic ether such as tetrahydrofurane, esters such as ethyl acetate or butyl acetate, or nitrites such as acetonitrile. Though there is no particular limitation, the reaction temperature may be from room temperature to about a boiling point of the solvent, and the reaction time may be from 0.5 hours to about 10 hours, which may be determined while making sure the progress of the reaction. Here, the protection group (substituted silyl group) may be removed depending upon the conditions, which, however, does not affect the subsequent steps. The thus obtained spirofluorenol of which the hydroxyl group is protected can be isolated and refined by conventional methods, but can also be directly used for the next reaction.

In the production method of the present invention, finally, the spirofluorenol of which the hydroxyl group and the like groups are protected obtained as described above is subjected to the removal of protection (removal of the substituted silyl group). Though there is no particular limitation, the method of removing the protection is easily conducted by the reaction with a protection-removing agent containing fluorine anions in a solvent.

As the protection-removing agent containing fluorine anions, there can be used quaternary ammonium fluorides such as tetrabutylammonium fluoride, benzyltrimethylammonium fluoride; and alkali metal fluorides such as sodium fluoride and potassium fluoride. When an alkali metal fluoride is used as the protection-removing agent, it is desired to also use a quaternary ammonium salt such as tetrabutylammonium bromide or benzyltrimethylammonium chloride in combination. There is no particular limitation on the solvent that is used provided it does not impair the reaction. Examples include acyclic or cyclic aliphatic hydrocarbons such as hexane and cyclohexane; aromatic hydrocarbons such as toluene and xylene; chlorinated hydrocarbons such as dichloromethane and chloroform; acyclic or cyclic ethers such as diethyl ether and tetrahydrofuran; nitrites such as acetonitrile and butyronitrile; alcohols such as methanol and ethanol; acyclic or cyclic amides such as dimethylformamide and N-methylpyrrolidone; acyclic or cyclic sulfoxide; sulfone such as dimethylsulfoxide and sulforane; or a mixed solvent thereof. These solvents may contain water.

In order to remove the protection, further, there can be easily employed a method of reacting the spirofluorenol of which the hydroxyl group and the like groups are protected with a compound of the above formula (4) together with alcohols or water. The solvent used here may be the above-mentioned solvent. Desirably, however, alcohols are used as a solvent so as to also serves as a reaction reagent.

It is also possible to remove the protection by using a Lewis acid such as boron trifluoride. There is no particular limitation on the solvent provided it is not decomposed by acid. Chlorinated hydrocarbons can be preferably used.

The spirofluorenol obtained by removing the protection can be isolated and refined according to conventional methods, but can also be directly used for the reaction for synthesizing a photochromic compound.

According to the production method of the present invention, further, it is possible to conduct the spiro-reaction and the protection-removing reaction in a single step by using an acid. Employment of this method is particularly preferred from the standpoint of improving the efficiency. In this case, preferred examples of the acid include organosulfonic acid, organic acid or Lewis acid and, particularly, p-toluene-sulfonic acid, trifluoroacetic acid, boron trifluoride (usually used as an ether complex), magnesium bromide or aluminum chloride among the acids exemplified above for being used for the spiro-reaction and the protection-removing reaction. There can be used any solvent without limitation provided it can be used for the spiro-reaction or the protection-removing reaction. From the standpoint of selectivity of the reaction, however, acetonitrile is most desired. After the reaction, the acid is inactivated and is washed by adding water or a saline solution thereto and, then, the solvent is removed from the organic layer to thereby obtain an object product.

The production method of the present invention makes it possible to efficiently produce the spirofluorenol compound useful as a starting material for producing a photochromic compound.

EXAMPLES

The present invention will now be described in detail by way of Working Examples to which only, however, the invention is in no way limited.

Example 1

2 Grams (6.5 mmols) of a 3,9-dimethoxy-5-hydroxy-benzo[c]fluorene-7-one was suspended in 10 ml of a tetrahydrofuran (THF) followed by the addition of a methanol solution (40 ml) containing 0.31 g (7.8 mmols) of sodium hydroxide, and the mixture was stirred at room temperature for one hour. After 80 ml of toluene was added, the solvent was all distilled off under a reduced pressure to obtain a sodium salt. The sodium salt was dissolved in 50 ml of the THF, and a THF (20 ml) solution containing 1.2 g (7.8 mmols) of a t-butyldimethylsilyl chloride was added dropwise thereto to conduct the reaction at room temperature for 2 hours. The conversion was 99%.

Then, the THF was distilled off under a reduced pressure, and 2.4 g of a 3,9-dimethoxy-5-t-butyldimethylsilyloxy-benzo [c] fluorene-7-one (purity, 97%; yield, 87%)(abbreviated as DBBF) was crystallized from 30 ml of methanol.

2.1 Grams (8.3 mmols) of a 1-bromophenanthrene was dissolved in 43 ml of heptane, 5.3 ml (1.6 mols/l, 8.5 mmols) of butyl lithium was added thereto at room temperature to obtain a 1-lithiophenanthrene, which was cooled down to −5° C., followed by the addition of 2.2 g (5.2 mmols) of the above DBBF. The mixture was stirred for one hour and to which was further added the THF at a temperature of not higher than 0° C. The mixture was stirred at this temperature for 2 hours. The conversion was 99%.

After the reaction, the reaction product was washed with 8.5 ml of 1N hydrochloric acid and 10 ml of water, and the solvent was distilled off under a reduced pressure. 2.5 Grams of a 3,9-dimethoxy-5-t-butyldimethylsilyloxy-7-hydroxy-7-phenanthrene-1-ylbenzo[c]fluorene (purity, 97%; yield, 82%)(abbreviated as DBHPBF) was crystallized from 20 ml of methanol.

Of the obtained 2.5 g of DBHPBF, 1.0 g (1.7 mmols) thereof was suspended in 10 g of acetic acid and was heated at 60° C. Here, a solution comprising 3.5 g of acetic acid, 0.7 g of concentrated sulfuric acid and 2.1 g of water was added thereto, and the mixture was stirred at 60° C. for 3 hours. The conversion was 99%.

The mixture was, then, cooled, adding 50 ml of THF and washed with 46 ml of a 5N sodium hydroxide aqueous solution, and was further washed two times each with 20 ml of water, and the solvent was distilled off under a reduced pressure. 0.87 Grams of a 3',9'-dimethoxy-5'-t-butyldimethylsilyloxyspiro [(1H-cyclopent[d,e,f]phenanthrene)-1,7'-benzo[c]fluorene] (purity, 96%; yield, 90%)(abbreviated as DBCPBF) was crystallized from 30 ml of methanol.

Of the obtained 0.87 g of DBCPBF, 0.58 g (1.0 mmol) thereof was dissolved in 30 ml of the THF, followed by the addition of 1.3 g (4 mmols) of a tetrabutylammonium bromide and 0.23 g (4 mmols) of potassium fluoride, and the mixture was heated and refluxed for 10 hours. The conversion was 98%. The mixture was cooled and was washed three times each with 10 ml of water, and the solvent was distilled off under a reduced pressure. 0.47 Grams (yield, 100%) of a 3',9'-dimethoxy-5'-hydroxyspiro[(1H-cyclopent[d,e,f]phenanthrene)-1,7'-benzo[c]fluorene] having a purity of 95% was obtained. The total yield was calculated to be 64%.

Comparative Example 1

0.28 Grams (7 mmols) of sodium hydroxide was dissolved in 20 ml of methanol, and to which were added 2 g (6.6 mmols) of a 3,9-dimethoxy-5-hydroxybenzo[c]fluorene-7-one, 0.82 g (6.5 mmols) of a benzyl chloride and 20 ml of the THF, and the mixture was refluxed for 20 hours. The conversion was 90%. A by-product was formed during the reaction presumably due to the reaction of two benzyl groups. The solvent was distilled off under a reduced pressure, and 1.4 g of a 3,9-dimethoxy-5-benzyloxybenzo[c]fluorene-7-one (purity, 97%; yield, 52%) was crystallized from 32 ml of acetone.

The phenanthrene addition reaction and the dehydration reaction were conducted in accordance with Example 1 to obtain a 3',9'-dimethoxy-5'-benzyloxyspiro[(1H-cyclopent[d,e,f]phenanthrene-1,7'-benzo[c]fluorene](abbreviated as spirobenzofluorene). The purity and the yield were 85% and 90%, respectively.

0.67 Grams (1.2 mmols) of the obtained spirobenzofluorene was dissolved in 30 ml of THF and 50 ml of methanol, and to which were added 0.27 g of 5% palladium on charcoal and 15.1 g (240 mmols) of ammonium formate, to conduct the reaction at room temperature for 2 hours. The conversion was 99%. After the reaction, palladium on charcoal was separated by filtration, washed with 20 ml of water, and the solvent was distilled off under a reduced pressure. 0.55 Grams (yield, 99%) of a 3',9'-dimethoxy-5'-hydroxyspiro [(1H-cyclopent[d,e,f])phenanthrene]-1,7'-benzo[c]fluorene] having a purity of 98% was obtained. The total yield was calculated to be 39%.

Comparative Example 2

10 Grams (32.6 mmols) of a 3,9-dimethoxy-5-hydroxybenzo[c]fluorene-7-one was suspended in 500 ml of the THF followed by the addition of 10.7 g (49 mmols) of a di-t-butyl dicarbonate and 0.04 g (0.3 mmols) of a 4-dimethylaminopyridine, and the mixture was stirred at room temperature for 3 hours. The THF was concentrated until crystals precipitated, and to which was added 400 ml of heptane to crystallize 12.8 g of a 3,9-dimethoxy-5-t-butoxycarbonyloxybenzo[c]fluorene-7-one (abbreviated as benzofluorenone)(purity, 96%; yield 97%).

The above benzofluorenone was reacted with the 1-lithiophenanthrene in the same manner as in Example 1, whereby the t-butoxycarbonyl group has reacted and the purity has dropped down to 61%. The dehydration reaction was conducted in the same manner as in Example 1, and it was found that the protection-removing reaction has occurred simultaneously. However, A 3',9'-dimethoxy-5'-hydroxyspiro[(1H-cyclopent[d,e,f]phenanthrene)-1,7'-benzo[c]fluorene] having a purity of only 44% was obtained. This compound could not be refined. Or, if it were refined without loss, the whole yield was calculated to be 43%.

Example 2

10 Grams (36.2 mmols) of a 3-methoxy-5-hydroxybenzo[c]fluorene-7-one was suspended in 150 ml of the THF followed by the addition of 4.4 g (43.5 mmols) of a triethylamine. Then, a solution obtained by dissolving 6.55 g (43.5 mmols) of a t-butyldimethylsilyl chloride in 50 ml of the THF was added thereto dropwise at room temperature, and the mixture was stirred at 45° C. for 6 hours. The conversion was 98%. The THF was distilled off under a reduced pressure and crystallize 12 g of a 3-methoxy-5-t-butyldimethylsilyloxybenzo[c]fluorene-7-one (abbreviated as MBBF)(purity, 98%; yield, 85%) from 230 ml of methanol.

10.9 Grams (38.9 mmols) of a 2-biphenyl iodide was dissolved in 150 ml of heptane and was cooled down to −5° C. 26.5 ml (1.6 mols/l, 42.4 mmols) of butyl lithium was added thereto, and the mixture was stirred at −5° C. for one hour. 10.5 Grams (27 mmols) of MBBF prepared above was added thereto, and the THF was added thereto at a temperature of not higher than 0° C., and the mixture was stirred at this temperature for 2 hours. The conversion was 99%. After the reaction, 200 ml of the THF was added to the reaction product and obtained solution was washed with 42 ml of 1N hydrochloric acid, and was further washed twice each with 50 ml of water. The solvent was distilled off under a reduced pressure to obtain 14 g of a 3-methoxy-5-t-butyldimethylsilyloxy-7-hydroxy-7-(2-phenylphenyl)benzo[c]fluorene (abbreviated as MBHPBF)(purity, 95%; yield, 95%).

Of the obtained 14 g of MBHPBF, 10.9 g (20 mmols) thereof was suspended in 115 g of acetic acid and was heated at 60° C. Here, a solution comprising 55 g of acetic acid, 10.9 g of concentrated sulfuric acid and 32.6 g of water was added thereto, and the mixture was stirred at 60° C. for 3 hours. The conversion was 99%. The mixture was, then, cooled down to 30° C. and 400 ml of ethyl acetate was added thereto, and obtained solution was washed with 740 ml of a 5N sodium hydroxide aqueous solution, and was further washed 200 ml of a 10% saline solution. The solvent was distilled off to obtain 10 g of a 3'-methoxy-5'-t-butyldimethylsilyloxyspiro[fluorene-9,7'-benzo[c]fluorene](abbreviated as MBSFBF)(purity, 95%; yield, 95%).

Of the obtained 10 g of MBSFBF, 0.53 g (1 mmol) thereof was dissolved in 30 ml of the THF, followed by the addition of 1.52 g (10 mmols) of a 1,8-diazabicyclo[5,4,0]undeca-7-one, and the mixture was stirred at room temperature for 24 hours. The conversion was 99%. The reaction product was, then, washed with 10 ml of 1N hydrochloric acid and was further washed three times each with 10 ml of water. The THF was distilled off to obtain 0.41 g of a 3'-methoxy-5'-hydroxyspiro[fluorene-9,7'-benzo [c]fluorene](purity, 96%; yield, 99%). The total yield was calculated to be 76%.

Example 3

A 3'-methoxy-5'-t-butyldimethylsilyloxyspiro [fluorene-9,7'-benzo[c]fluorene](abbreviated as MBSFBF) was obtained in compliance with Example 2.

0.53 Grams (1 mmol) of the above MBSFBF was dissolved in 30 ml of chloroform, cooled down to 5° C., and to which was added 3.4 g (24 mmols) of a diethyl ether complex of boron trifluoride to conduct the reaction at 50° C. for 20 hours. The conversion was 99%. Thereafter, the reaction product was cooled and washed with 24 ml of 1N sodium hydroxide aqueous solution and four times each with 50 ml of water.

The chloroform was distilled off to obtain 0.40 g of a 3'-methoxy-5'-hydroxyspiro[fluorene-9,7'-benzo[c]fluorene](purity, 96%; yield 97%). The total yield was calculated to be 74%.

Comparative Example 3

0.4 Grams (10 mmols) of sodium hydroxide was dissolved in 10 ml of methanol, and to which were added 2.5 g (9.1 mmols) a 3-methoxy-5-hydroxybenzo[c]fluorene-7-one, 30 ml of the THF and 3.7 g (29 mmols) of a benzyl chloride, and the mixture was stirred at 60° C. for 10 hours. The conversion was 95%.

Thereafter, the mixture was cooled down to 20° C., and the precipitated crystals were filtered, washed with 10 ml of water, and were dried to obtain 2.0 g of a 3-methoxy-5-benzyloxybenzo[c]fluorene-7-one (purity, 99%; yield, 61%).

The biphenyl addition reaction and the dehydration reaction were conducted in accordance with Example 2 to obtain 2.5 g of a 3'-methoxy-5'-benzyloxyspiro[fluorene-9,7'-benzo[c]fluorene](abbreviated as MBOSFBF). The purity and the yield were 97% and 95%, respectively.

0.5 Grams (1 mmol) of the above MBOSFBF was dissolved in a mixed solvent of 50 ml of THF, 10 ml of acetic acid, 5 ml of methanol and 1.5 ml of water, and to which was added 0.05 g of 5% palladium on charcoal. The mixture was stirred under hydrogen atmosphere by using a hydrogen balloon at 40° C. for 24 hours. The conversion was 99%. After the reaction, the reaction product was cooled, palladium on charcoal was separated by filtration, and the solvent was removed by distillation under a reduced pressure to obtain 0.41 g of a 3'-methoxy-5'-hydroxyspiro[fluorene-9,7'-benzo[c]fluorene](purity, 98%; yield, 98%). The total yield was calculated to be 55%.

Example 4

A 3,9-dimethoxy-5-t-butyldimethylsilyloxy-7-hydroxy-7-phenanthrene-1-ylbenzo[c]fluorene](abbreviated as DBHPBF) was obtained in compliance with Example 1.

1.0 Gram (1.7 mmols) of the above DBHPBF was dissolved in 70 ml of acetonitrile, and to which was added 0.71 g (5 mmols) of an ether complex of boron trifluoride, and the mixture was stirred at 50° C. for 3 hours. 0.32 Grams (5.5 mmols) of potassium fluoride was added to inactivate the ether complex of boron trifluoride and, after 90 ml of THF was added, the reaction product was washed three times each with 80 ml of a 10% of saline solution. The solvent was distilled off under a reduced pressure to obtain 0.46 g (yield, 98%) of a 3',9'-dimethoxy-5'-hydroxyspiro[(1H-cyclopent[d,e,f]phenanthrene)-1,7'-benzo[c]fluorene] having a purity of 98%. The total yield was calculated to be 63%.

Examples 5 to 11

The 3,9-dimethoxy-5-t-butyldimethylsilyloxy-7-hydroxy-7-phenanthrene-1-ylbenzo[c]fluorene was subjected to the spiro-reaction and to the protection-removing reaction in compliance with Example 4 under the conditions shown in Table 1 to obtain the results shown in Table 1.

Comparative Example 4

2.1 Grams (8.3 mmols) of a 1-bromophenanthrene was dissolved in 43 ml of heptane, and to which was added 5.3 ml (1.6 mols/l, 8.5 mmols) of butyllithium to obtain a 1-lithiophenanthrene, which was, then, cooled down to −5° C. 1.6 Grams (5.2 mmols) of the 3.9-dimethoxy-5-hydroxybenzo[c]fluorene-7-one was added thereto, and the mixture was stirred for one hour. Then, THF was added thereto at a temperature of not higher than 0° C., and the mixture was stirred at this temperature for 2 hours. The conversion was 40%. The mixture was continuously stirred for another 20 hours, but the conversion remained to be 40%.

After the reaction, the reaction product was washed with 8.5 ml of 1N hydrochloric acid and 10 ml of water, and the solvent was distilled off under a reduced pressure. 0.81 Grams of a 3,9-dimethoxy-5-hydroxy-7-hydroxy-7-phenanthrene-1-ilbenzo[c]fluorene(abbreviated as DHHPBF)(purity, 92%; yield, 32%) was crystallized from 20 ml of methanol.

Of the obtained DHHPBF, 0.5 g (1.0 mmol) thereof was suspended in 5.9 g of acetic acid, and was heated at 60° C. A solution comprising 2.1 g of acetic acid, 0.4 g of concentrated sulfuric acid and 1.2 g of water was added thereto, and the mixture was stirred at 60° C. for 3 hours. The conversion was 99%.

Then, the mixture was cooled and was washed with 27 ml of 5N sodium hydroxide and 30 ml of THF, and was further washed twice each with 13 ml of water, and the solvent was distilled off under a reduced pressure. 0.2 Grams of a 3',9'-dimethoxy-5'-hydroxyspiro[(1H-cyclopent[d,e,f]phenanthrene)-1,7'-benzo[c]fluorene] was crystallized from 17 ml of methanol (purity 95%; yield, 40%). The total yield was calculated to be 13%.

TABLE 1

| Example No. | Starting material (mmol) | Solvent (60 ml) | Acid | Amount of acid (mmol) | Temperature (° C.) | Time (hr) | Purity (%) | Yield (%) |
|---|---|---|---|---|---|---|---|---|
| 5 | 1.67 | acetonitrile | boron trifluride ether complex | 16.7 | 25 | 10 | 97 | 97 |
| 6 | 1.67 | acetonitrile | p-toluene-sulfonic acid | 5.3 | 50 | 3 | 97 | 96 |
| 7 | 1.67 | acetonitrile | magnesium bromide | 54.3 | 50 | 3 | 98 | 98 |
| 8 | 1.67 | THF | trifluoroacetic acid | 6.5 | 40 | 1 | 96 | 95 |
| 9 | 1.67 | acetonitrile | aluminum chloride | 16.7 | 25 | 10 | 97 | 97 |
| 10 | 1.67 | ethyl acetate | titanium tetrachloride | 16.7 | 25 | 10 | 96 | 96 |

TABLE 1-continued

| Example No. | Starting material (mmol) | Solvent (60 ml) | Acid | Amount of acid (mmol) | Temperature (° C.) | Time (hr) | Purity (%) | Yield (%) |
| --- | --- | --- | --- | --- | --- | --- | --- | --- |
| 11 | 1.67 | acetonitrile | silicon tetrachloride | 8.4 | 50 | 5 | 96 | 96 |

The invention claimed is:

1. A method of producing a spirofluorenol compound represented by the following formula (1),

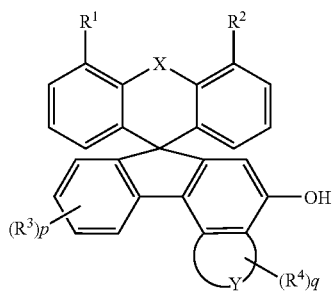

(1)

by protecting a hydroxyl group bonded to a fluorenone compound represented by the following formula (2),

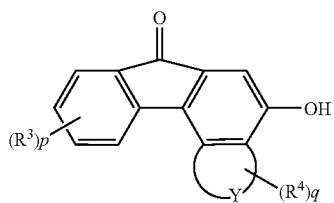

(2)

with a protecting group which is a substituted silyl group in which the sum of carbon atoms of substituents bonded to a silicon atom is 5 to 12, then, reacting the fluorenone compound with an organometal compound represented by the following formula (3),

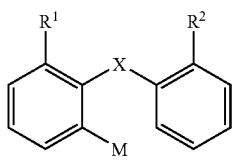

(3)

wherein M is Li, MgCl, MgBr, MgI or CuLi,
to thereby obtain a hydroxy-arylfluorenol of which the hydroxyl group is protected with said protecting group, and transforming the obtained hydroxy-arylfluorenol into a spiro form and removing the protection therefrom, wherein in the above formulas (1) to (3):

X is either a single bond or a divalent group selected from the following group A;

Y is a group forming an aromatic hydrocarbon cyclic group or an unsaturated heterocyclic group together with two carbon atoms of a benzo ring;

when X is a single bond, $R^1$ and $R^2$ are, respectively, hydrogen atoms or monovalent groups selected from the following group B, or are bonded together to form a divalent group selected from the following group A (except, -Z- and $-CR^5R^6-$);

when X is a group selected from the group A, $R^1$ and $R^2$ are, respectively, hydrogen atoms or monovalent groups selected from the following group B;

$R^3$ and $R^4$ are, respectively, hydrogen atoms or monovalent groups selected from the following group B; and p and q are, independently from each other, integers of 0 to 3;

group A:

-Z-, $-(CR^5R^6)_n-$, $-(CR^5R^6)_m-Z-$, $-Z-(CR^5R^6)_l-Z-$, $-(CR^5R^6)_a-Z-(CR^5R^6)_b-$, $-(CR^5=CR^6)_k-$, and $CR^5=N-$ wherein -Z- is $-O-$, $-S-$ or $-NR^5-$, $R^5$ and $R^6$ are, independently from each other, hydrogen atoms, or monovalent groups selected from the following group B, wherein when there are a plurality of -Z-, $R^5$ or $R^6$ in one group, the plurality of -Z-, $R^5$ or $R^6$ may be different from each other, and a, b, k and l are, independently from each other, integers of 1 to 4, and m and n are, independently from each other, integers of 1 to 6;

group B:

alkyl group, aralkyl group, substituted or unsubstituted aryl group, hydroxy group, alkoxy group, aralkoxy group, amino group, monosubstituted amino group, disubstituted amino group, cyano group, nitro group, halogen atom, trufluoromethyl group, substituted or unsubstituted heterocyclic group having a bond on a carbon atom or on a nitrogen atom, and substituted or unsubstituted condensed heterocyclic group to which aromatic hydrocarbon ring or hetero ring is condensed and having a bond on a carbon atom or on a nitrogen atom.

2. A production method according to claim 1, wherein when the fluorenone compound represented by the above formula (2) has an amino group or a monosubstituted amino group, said hydroxyl group as well as said amino group or said monosubstituted amino group are protected with said protecting groups.

3. A production method according to claim 1, wherein the protection by using said substituted silyl group is conducted in the presence of a compound represented by the following formula (4),

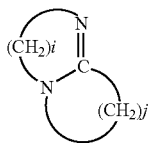 (4)

wherein i is an integer of 2 to 4, and j is an integer of 3 to 6.

4. A production method according to claim 1, wherein the protection is removed from the spirofluorenol by the reaction with a quaternary ammonium fluoride or with a fluoride of an alkali metal, said spirofluorenol being obtained by transforming the hydroxy-arylfluorenol protected by said protecting group into a spiro form.

5. A production method according to claim 3, wherein the protection is removed from the spirofluorenol by the reaction with an alcohol or with water in the presence of the compound represented by the above formula (4), said spirofluorenol being obtained by transforming the hydroxy-arylfluorenol protected by said protecting group into a spiro form.

6. A production method according to claim 1, wherein the hydroxy-arylfluorenol protected by said protection group is transformed into a spiro form and from which the protection is removed in one step by being reacted with an acid in an acetonitrile solvent.

7. A production method according to claim 6, wherein, as the acid, there is used at least the one compound selected from the group consisting of boron trifluoride ether complex, magnesium bromide, paratoluenesulfonic acid, aluminum chloride and trifluoroacetic acid.

* * * * *